(12) United States Patent
Pulliainen et al.

(10) Patent No.: US 6,365,035 B1
(45) Date of Patent: Apr. 2, 2002

(54) METHOD FOR MEASURING PROPERTIES OF THE STACK AND THE CORROSION OF MATERIALS IN A SODA RECOVERY UNIT

(75) Inventors: Martti Pulliainen, Anttola; Timo Laurila, Lahti; Arttu Laitinen, Espoo; Antero Heinävaara, Kaskinen, all of (FI)

(73) Assignee: Savcor Consulting Oy, Mikkeli (FI)

( * ) Notice: Subject to any disclaimer, the term of this patent is extended or adjusted under 35 U.S.C. 154(b) by 0 days.

(21) Appl. No.: 09/530,715
(22) PCT Filed: Nov. 3, 1998
(86) PCT No.: PCT/FI98/00849
 § 371 Date: Jun. 30, 2000
 § 102(e) Date: Jun. 30, 2000
(87) PCT Pub. No.: WO99/23481
 PCT Pub. Date: May 14, 1999

(30) Foreign Application Priority Data

Nov. 4, 1997 (FI) .................................................. 974122

(51) Int. Cl.[7] .............................................. G01N 27/26
(52) U.S. Cl. ................................ 205/775.5; 205/793.5; 204/404; 73/DIG. 9
(58) Field of Search ................................ 204/400, 401, 204/404, 422, 423; 205/775, 775.5, 781.5, 793.5; 324/439, 72, 72.5; 73/866, DIG. 9

(56) References Cited

U.S. PATENT DOCUMENTS

| 4,599,975 A | 7/1986 | Reeve et al. ................. 122/379 |
| 4,627,905 A | 12/1986 | Garner et al. ................ 204/404 |
| 4,683,841 A | 8/1987 | Andersson et al. ........... 122/22 |
| 5,010,827 A | 4/1991 | Kychakoff et al. .......... 110/185 |

OTHER PUBLICATIONS

Copy of PCT International Search Report.

*Primary Examiner*—T. Tung
*Assistant Examiner*—Alex Noguerola
(74) *Attorney, Agent, or Firm*—Steinberg & Raskin, P.C.

(57) ABSTRACT

The invention relates to a method for measuring the properties of a stack (15) that viscous molten salt forms on the bottom of a soda recovery unit (14) while black liquor is burned therein, and for measuring the corrosion of the materials of construction of the unit (14) during the operation thereof. In the method, at least one sensor means (11) is brought into contact with said stack (15), this sensor means (11) being electrically insulated from the soda recovery unit (14). In the method, at least some electrochemical properties and the temperature of said stack (15) are measured with this sensor means (11). The data measured with this sensor means (11) are fed to a measuring and data acquisition unit (12), and said measuring and data acquisition unit (12) is controlled by a control unit (13).

4 Claims, 1 Drawing Sheet

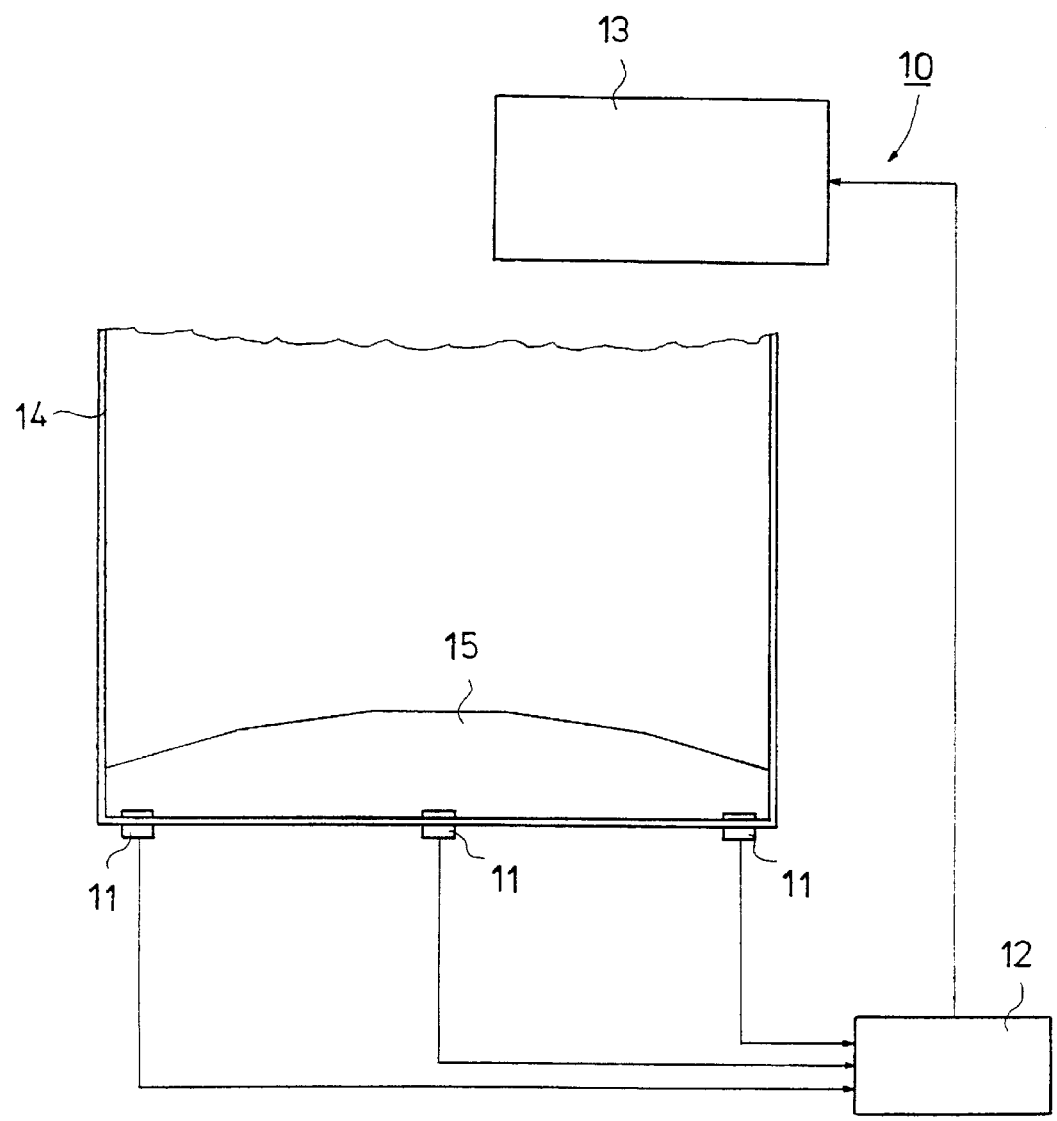

METHOD FOR MEASURING PROPERTIES OF THE STACK AND THE CORROSION OF MATERIALS IN A SODA RECOVERY UNIT

FIELD OF THE INVENTION

The present invention relates to a method for measuring the properties of a stack that viscous molten salt forms on the bottom of a soda recovery unit while black liquor is burned therein, and for measuring the corrosion of the materials of construction of the unit during the operation thereof.

BACKGROUND OF THE INVENTION

In general, the properties of the stack and the corrosion of materials are determined by using known electrochemical measuring methods, for instance to measure the potential, polarization resistance, impedance and resistivity, together with the temperature.

The soda recovery unit, in which black liquor formed in the cooking step of sulphate pulp is burned, produces electric energy (about 40% of the total requirement) and steam needed in a pulp plant. On the other hand, the chemicals necessary for pulp cooking are regenerated in the soda recovery unit. As the black liquor is burned in the unit, a stack of viscous molten salt is formed on the bottom thereof. The control of this stack is of paramount importance to the balance and stability of the process, which in turn are prerequisites for the effective energy production and regeneration of chemicals. In addition, any changes in the stack have an influence on the service life of the piping on the bottom of the soda recovery unit.

In a pulp plant, the soda recovery unit is the most expensive, and probably the most critical unit, and thus the greatest safety risk. Inappropriate operation of the unit for any reason affects the whole plant. Irregular burning in the soda recovery unit leads to a decreased steam production, and due to this, the lacking amount of steam must be produced with an auxiliary unit. Because insufficient amounts of steam, and accordingly electricity are produced, more electricity has to be purchased from outside the plant. Process failures in the soda recovery unit interfere with the regeneration of the chemicals and increase air pollution. All these factors decrease directly or indirectly the productivity of the pulp plant. If the operation failure is severe enough to make the running down of the soda recovery unit necessary, then the pulp plant as a whole must be run down. For the plant, the economic losses due to this may amount each day on average to USD 300.000.

More serious than operation failures is an eventual damage of the piping under the stack, at the bottom of the unit. Normally, a solidified salt layer protects the bottom piping, but the properties of this protective layer may vary, or the layer may be absent altogether, for instance due to a shutdown of the unit or a process failure. The bottom piping of the unit may then be exposed to the molten salt. Molten salt is extremely corrosive, damaging and even giving rise to holes through the walls of the bottom piping. Water enters the stack through these holes, causing the risk of a so called melt water explosion that may damage the whole unit and cause economic losses summing up even to several millions of US dollars due to mere material damage, without considering production losses at all. In addition, the explosion may be so violent that even casualties are possible.

In the future, process conditions are becoming increasingly complicated due to more and more restrictive requirements concerning industrial production, recycling, and environment. The result has already been an increased corrosion in the soda recovery unit. Repairing the unit, and accordingly production losses due to extraordinary, or prolonged shutdowns, as well as additional inspection and maintenance may cost the plant several millions or tens of millions of dollars yearly. Recently, of particular concern has been the cracking of the bottom piping made of so called compound material. It is known that in Finland about 50% of the bottom piping made of this compound material have cracks. This cracking has been studied worldwide for several years without learning any actual reasons for it. Indeed, the bottle neck of the production of a pulp plant may in the future be the soda recovery unit which may not be operated with full capacity because of inadequate knowledge about the behavior of the stack and corrosion of the bottom piping material in these new process conditions.

At present, no system allowing the monitoring of the properties of the stack by direct measurements is available for controlling the soda recovery unit. Moreover, there are no apparatus for estimating the resistance of the construction materials and studying them in the actual environment in the unit. For the time being, the stack may only be monitored with cameras provided in the fire chamber, and with pyrometers measuring the temperature of the outer surface of the stack, but they do not give any data from within the stack. The bottom piping of the unit may at present be equipped with thermoelements for measuring the temperature, and the piping may be coated with a paint reacting to temperature changes, but, however, the information obtained with these methods is not sufficient as such to control the process, or especially to study the resistance of the materials of construction.

Indeed, the state of the art provides neither a suitable method, nor an apparatus for measuring the properties of the stack in a soda recovery unit, or studying and testing the resistance of materials in the actual conditions prevailing in the unit.

OBJECTS AND SUMMARY OF THE INVENTION

The object of the present invention is to provide a method for improving the controllability and safety of a soda recovery unit. More particularly, the object of the invention is to provide a method for measuring the properties of the stack in the soda recovery unit and the corrosion of construction materials thereof during operation, this method further taking advantage of the measured data to control directly or indirectly the soda recovery process.

BRIEF DESCRIPTION OF THE DRAWINGS

The FIGURE of the drawing shows schematically an apparatus used in the method of the invention to measure the properties of the stack in a soda recovery unit, and corrosion of materials of construction during the operation thereof.

DETAILED DESCRIPTION OF THE INVENTION

The object of the present invention is achieved with a method, which is characterized in that it comprises the following steps wherein (a) at least one sensor element is brought into contact with said stack, that this sensor element being electrically insulated from the soda recovery unit;

(b) at least some electrochemical properties and the temperature of said stack are measured with this sensor element;

(c) the data obtained with this sensor element are fed to a measuring and data acquisition unit; and (d) a control unit controls said measuring and data acquisition unit.

In the method of the present invention, generally known electrochemical measuring methods and temperature measurements may be utilized to determine the properties of the stack in said soda recovery unit environment, during the operation of the unit.

In the method according to the invention, the soda recovery unit is provided with at least one sensor, preferably several sensors brought into contact with the stack. The sensors are insulated electrically from the recovery unit, and they are designed to resist high temperatures and the corrosive environment in the stack. In these electrochemical measuring methods, either the free potential is measured, or electric current is fed to the sensors and the potential changes of the sensors due to this current are measured. The temperature is measured with conventional thermoelements.

The method of the present invention is useful for monitoring soda recovery units.

The invention will now be illustrated in more detail with reference to the figure of the appended drawing, showing a preferable embodiment of the invention, without intending to limit the invention solely thereto.

In the figure, said apparatus is generally referred to with the numeral 10. The apparatus 10 comprises a sensor 11 for both electrochemical and temperature measurements, a measuring and data acquisition unit 12, and a control unit 13. The soda recovery unit is referred to with the numeral 14, and the numeral 15 refers to the stack formed on the bottom thereof.

Disturbances in the soda recovery unit process have a significant effect on the results of the electrochemical measurement. In the first place, changes in the operation parameters of said unit become immediately apparent from increased electrochemical noise. Further, said changes in the operation parameters cause a decrease in the polarization resistance of steel, which may be considered as an indication of a more corrosive environment. Such changes in the operation parameters also bring about changes in the resistivity of the stack, possibly indicating the formation of a so called melt phase in the stack. It is assumed that the formation of a melt phase is a reason for the corrosion and damage of the piping on the bottom of the unit.

Only the principle of the invention is disclosed above, and it is apparent to a person skilled in the art that several modifications are possible without departing from the spirit and scope of the invention.

What is claimed is:

1. A method for measuring properties of a stack that viscous molten salt forms on the bottom of a soda recovery unit when black liquor is burned therein, and for measuring the corrosion of materials of construction of the recovery unit, wherein the method comprises the steps of:

arranging sensing means in contact with the stack, wherein the sensing means is electrically insulated from the soda recovery unit;

measuring at least one electrochemical property and the temperature of said stack;

feeding data obtained from measuring at least some electrochemical properties and the temperature of said stack to a measuring and data acquisition unit and; and controlling the measuring and data acquisition unit by a control unit.

2. A method according to claim 1, further comprising the step of adjusting the operational parameters controlling the operation of said soda recovery unit based on said data obtained from measuring at least one electrochemical property and the temperature of said stack.

3. A method according to claim 1, further comprising the step of using said data obtained from measuring at least one electrochemical property and the temperature of said stack in controlling said soda recovery unit.

4. A method according to claim 1, further comprising the step of predicting the resistance of the materials of construction of said recovery unit based on said data obtained from measuring at least one electrochemical property and the temperature of said stack.

* * * * *

UNITED STATES PATENT AND TRADEMARK OFFICE
CERTIFICATE OF CORRECTION

PATENT NO. : 6,365,035 B1  Page 1 of 1
DATED : April 2, 2002
INVENTOR(S) : Pulliainen et al.

It is certified that error appears in the above-identified patent and that said Letters Patent is hereby corrected as shown below:

<u>Title page,</u>
Item [73], should read as follows: -- Savcor Process Oy --

Signed and Sealed this

Twentieth Day of August, 2002

Attest:

Attesting Officer

JAMES E. ROGAN
*Director of the United States Patent and Trademark Office*